United States Patent [19]
Hong et al.

[11] Patent Number: 5,834,253
[45] Date of Patent: *Nov. 10, 1998

[54] BACILLUS STEAROTHERMOPHILUS DNA POLYMERASE WITH PROOF-READING 3'-5' EXONUCLEASE ACTIVITY

[75] Inventors: Guo Fan Hong, Shanghai; Wei-hua Huang, Zhejiang; Feng Zhai, deceased, late of Shanghai, all of China, by Fudi Ni, executor

[73] Assignee: Shanghai Institute of Biochemistry, Chinese Academy of Sciences, Shanghai, China

[*] Notice: The term of this patent shall not extend beyond the expiration date of Pat. No. 5,747,298.

[21] Appl. No.: 642,684

[22] Filed: May 3, 1996

Related U.S. Application Data

[63] Continuation-in-part of Ser. No. 544,643, Oct. 18, 1995.

[30] Foreign Application Priority Data

Nov. 17, 1994 [CN] China .............................. 94-1-13990.5

[51] Int. Cl.⁶ .............................. C12N 9/12; C12N 15/54; C12P 19/34
[52] U.S. Cl. ..................... 435/91.1; 435/194; 435/252.3; 435/252.5; 435/325; 435/419; 536/23.2
[58] Field of Search .................................. 435/194, 91.1, 435/252.5, 252.3, 6, 325, 419; 536/23.2

[56] References Cited

PUBLICATIONS

Riggs et al., Construction Of Single Amino Acid Substitution Mutants Of loned *Bacillus Stearothermophilus* DNA Polymerase I Which Lacks 3'–5' Exonuclease Activity, Biochimica et Biophysica Acta 1307 (1996), pp. 178–86.

Aliotta et al., Thermostable Bst DNA Polymerase I Lacks A 3'–5' Proofreaidng Exonuclease Activity, Genetic Analysis Biomolecular Engineering, 12 (1996), pp. 185–95.

Sanger et al., DNA Sequencing With Chain–Terminating Inhibitors, Biochemistry: Proc. Natl. Acad. Sci. USA 74 (1977), pp. 5463–5467.

Okazaki et al., Enzymatic Synthesis Of Deoxyribonucleic Acid, The Journal of Biological Chemistry, Vo. 239, No. 1, Jan. 1964, pp. 259–568.

Shengyu et al., Heat–Stable DNA Polymerase I Large Fragment Resolves Hairpin Structure In DNA Seuencing, Scientia Sinica (Series B), Vol. XXX, No. 5, May 1987, pp. 503–506.

Jacobsen et al., The N–Terminal Amino–Acid Sequences Of DNA Polymerase I From *Escherichia Coli* And Of The Large And The Small Fragments Obtained By A Limited Proteolysis, Eur. J. Biochem. 45 (1974), pp. 623–627.

McClary, et al., Sequencing With The Large Fragment Of DNA Polymerase I From Bacillus Stearothermophilus, DNA Sequence–J.DNA Sequencing and Mapping, Vol. 1 (1991) pp. 173–180.

John Wiley & Sons, Inc., DNA Sequencing, Current Protocols In Molecular Biology, Vol. 1 (1994).

Technical Bulletin, Promega, V. Sequence Of pGEM3z(+) ) Vector, Revised Feb.95, pp.5–6.

Mead et al., BST DNA Polymerase Permits Rapid Sequence Analysis From Nanogram Amounts Of Template, Biotechniques, Vol. 11, No. 1 (1991) pp. 76–84.

Earley et al., Robotic Automation Of Dideoxyribonucleotide Sequencing Reactions, Biotechniques, Vol. 17, No. 1 (1994) pp. 156–165.

Mardis et al., Automated Methods For Single–Stranded DNA Isolation And Dideoxynucleotide DNA Sequencing Reactions On A Robotic Workstation, Biotechniques, Vol. 7, No. 8 (1989) pp. 840–850.

What's New In This Catalog?, Isotherm ™ DNA Polymerase ((rBST DNA Polymerase Large Fragment), Epicentre Technologies Corporation (1994) p. 1.

Bio Rad, Pre–Mixed Nucleotide Sequencing Kits For BST$^{SM}$ DNA Polymerase, US Bulletin, p. 1649 (Date N.A.).

Bio Rad, Fluorescent–Abeled DNA Sequencing Reactions Using BST Polymerase 92, U.S. Bulletin 1771, pp. 1–4 (Date N.A.).

*Primary Examiner*—Keith D. Hendricks
*Attorney, Agent, or Firm*—Cushman Darby & Cushman IP Group of Pillsbury Madison & Sutro, LLP

[57] ABSTRACT

The invention relates to DNA polymerases which are capable of proofreading 3'-5' exonuclease activity during DNA sequencing of a DNA strand, such that the DNA polymerase functions to excise mismatched nucleotides from the 3' terminus of the DNA strand at a faster rate than the rate at which the DNA polymerase functions to remove nucleotides matched correctly with the nucleotides of the template, and which DNA polymerase does not exhibit 5'-3' exonuclease activity. The invention also relates to isolated and cloned DNA sequences derived from the *Bacillus stearothermophilus* thermostable DNA polymerase, as well as the expressed polymerase itself.

23 Claims, 2 Drawing Sheets

BACILLUS STEAROTHERMOPHILUS DNA POLYMERASE WITH PROOF-READING 3'-5' EXONUCLEASE ACTIVITY

This application is a continuation-in-part application of Ser. No. 08/544,643, filed Oct. 18, 1995, the entire contents of which are incorporated herein by reference.

BACKGROUND OF THE INVENTION

The genetic material of all known living organisms is deoxyribonucleic acid (DNA), except in certain viruses whose genetic material may be ribonucleic acid (RNA). DNA consists of a chain of individual deoxynucleotides chemically linked in specific sequences. Each deoxynucleotide contains one of the four nitrogenous bases which may be adenine (A), cytosine (C), guanine (G) or thymine (T), and a deoxyribose, which is a pentose, with a hydroxyl group attached to its 3' position and a phosphate group attached to its 5' position. The contiguous deoxynucleotides that form the DNA chain are connected to each other by a phosphodiester bond linking the 5' position of one pentose ring to the 3' position of the next pentose ring in such a manner that the beginning of the DNA molecule always has a phosphate group attached to the 5' carbon of a deoxyribose. The end of the DNA molecule always has an OH (hydroxyl) group on the 3' carbon of a deoxyribose.

DNA usually exists as a double-stranded molecule in which two antiparallel DNA strands are held together by hydrogen bonds between the bases of the individual nucleotides of the two DNA strands in a strictly matched "A-T" and "C-G" pairing manner. It is the order or sequence of the bases in a strand of DNA that determines a gene which in turn determines the type of protein to be synthesized. Therefore, the accurate determination of the sequence of the bases in a DNA strand which also constitutes the genetic code for a protein is of fundamental importance in understanding the characteristics of the protein concerned.

The process used to determine the sequence of the bases in a DNA molecule is referred to as DNA sequencing. Among the techniques of DNA sequencing, the enzymatic method developed by Sanger et al. (1) is most popular. It is based on the ability of a DNA polymerase to extend a primer annealed to the DNA template to be sequenced in the presence of four normal deoxynucleotide triphosphates (dNTPs), namely, dATP, dCTP, dGTP and dTTP, and on the ability of the nucleotide analogs, the dideoxynucleotide triphosphates (ddNTPs), namely, ddATP, ddCTP, ddGTP and ddTTP, to terminate the extension of the elongating deoxynucleotide polymers at various lengths.

In the classic one-step Sanger method, the sequence determination is carried out in a set of four separate tubes, each containing all four normal dNTPs, one of which is labeled with a radioactive isotope, $^{32}P$ or $^{35}S$, for autoradiographic localization, a limiting amount of one of the four ddNTPs, a DNA polymerase, a primer, and the DNA template to be sequenced. As a result of the DNA polymerase activity, individual nucleotides or nucleotide analogs are added to the new DNA chains, all starting from the 3' end of the primer in a 5'-3' direction, and each linked to adjacent ones with a phosphodiester bond in a base sequence complementary to the DNA sequence of the template. Inasmuch as there is a nucleotide analog in the reaction mixture, each tube eventually contains numerous newly formed DNA strands of various lengths, all ending in a particular ddNTP, referred to as A, C, G or T terminator.

After resolving the four sets of reaction products by high-resolution polyacrylamide/urea gel electrophoresis, the populations of the newly formed DNA strands are separated and grouped according to their molecular weight. An autoradiographic image of the gel will show the relative positions of these DNA strands as bands which differ from one another in distance measured by one nucleotide in length, all sharing an identical primer and terminating with a particular ddNTP (A, C ,G or T). By reading the relative positions of these bands in the "ladder" of the autoradiograph, the DNA sequence of the template can be deduced.

The DNA polymerase used in the reaction mixture plays a pivotal role in DNA sequencing analysis. To be useful for DNA sequencing, a DNA polymerase must possess certain essential properties. For example, it must have its natural 5'-3' exonuclease activity removed by mutagenesis or by posttranslational modification, such as enzymatic digestion, and must be able to incorporate dNTPs and ddNTPs, without undue discrimination against ddNTP and with a sufficiently high processivity which refers to the ability of the enzyme to polymerize nucleotides onto a DNA chain continuously without being dislodged from the chain, and a sufficiently high elongation rate. A 5'-3' exonuclease activity associated with a DNA polymerase will remove nucleotides from the primer, thus cause a heterogeneous 5' end for the newly formed DNA strands, resulting in a false reading of the strand lengths on the sequencing gel. A DNA polymerase with a low processivity and a low elongation rate will cause many undesirable noise background bands of radioactivity due to the presence of DNA strands which are formed with improper lengths and improper terminations. Among the more commonly used DNA polymerases, Sequenase has a higher processivity and a higher elongation rate than others, such as the Klenow fragment, Taq, and Vent polymerases (2), and is therefore one of the most popular DNA polymerase selected for DNA sequencing to-date.

However, even when a DNA polymerase has been endowed with all the essential properties listed above, it may still generate erroneous or misleading band patterns of radioactivity in the sequencing gel. These artifactual patterns do not faithfully reflect the true nucleotide sequence in the template being sequenced. They may be caused by premature termination of the elongating strands due to the presence of secondary structures formed along the template, such as "hairpins" in the regions that contain palindromic sequences or that are rich in G and C bases (3); or, they may occur as a result of inadequate "proof-reading" function of the DNA polymerase that will allow the removal of misincorporated nucleotides at the 3' end of an elongating strand.

Researchers in the field of DNA sequencing often have to use several approaches to confirm their findings in order to avoid being misled by these potentially erroneous sequence data. For example, they sometimes rely on repeating the same sequencing experiment with different DNA polymerases, or performing another sequencing reaction with the template which is complementary to the first single-stranded DNA template, and compare the results for possible discrepancies.

Numerous investigators have tried to find an ideal DNA polymerase for enzymatic sequencing, i.e. an enzyme that not only has all the essential properties required for sequencing reaction, but also is capable of resolving the secondary hairpin structures and preventing the formation of strands containing nucleotides non-complementary to those of the template being sequenced.

The discovery by Ye and Hong (4) of the thermostable large fragment of DNA polymerase isolated from *Bacillus stearothermophilus*, an enzyme that is functional over the temperature range between 25° C. and 75° C., but is most active at 65° C., and possesses all the essential properties for DNA sequencing, has largely solved the problem caused by secondary structures in the template since these secondary structures are destabilized when the sequencing reaction is carried out at 65° C. In the past few years since this enzyme was made commercially available under the name of Bst DNA Polymerase (Bio-Rad Laboratories), independent reports have confirmed that during sequencing reaction catalyzed by this enzyme all four dNTPs, including dCTP, and other nucleotide analogs, such as dITP and 7-deaza-dGTP, are incorporated equally effectively in the chain elongation, thus eliminating the weak "C" band phenomena often observed when other DNA polymerases are used, and producing a very good band uniformity on the sequencing gel. It has been further established that at this elevated temperature Bst DNA Polymerase system can be used both for the classic Sanger one-step reaction as well as for the "labeling/termination" sequencing reaction, double-stranded DNA sequencing, and the incorporation of $^{35}$S-labeled nucleotides, and $^{32}$P-labeled nucleotides. Since this system can be placed at room temperature for at least two weeks without significant loss of its enzymatic activity, it has been adapted for automation of DNA sequencing which requires a stable DNA polymerase, using either fluorescent dye or radioactive isotope labeling.

One problem with the Bst DNA polymerase currently known in the art is its lack of 3'-5' exonuclease activity (5), and specifically, proof-reading 3'-5' exonuclease activity. A survey of the sequencing data collected from fourteen research centers which have used this Bst DNA polymerase for their DNA sequencing work on over 120 DNA clones showed that, statistically, base pair mismatching occurs at a rate of about $1.5 \times 10^{-5}$. That is, approximately 1.5 errors can be expected in one hundred thousand nucleotide incorporations during nucleotide polymerization catalyzed by the enzyme.

It is generally known that the formation of incorrect DNA sequences due to mismatching of base pairs between the template and the growing nucleotide chain in DNA sequencing may be prevented by a 3'-5' exonuclease activity which "proof-reads" the nucleotide chain. However, even if a DNA polymerase exhibits 3'-5' exonuclease activity in vitro, it is often the case that the polymerase will not adequately "proof-read". Thus, the polymerase will not be capable of removing mismatched nucleotides from a newly formed DNA strand as efficiently as those nucleotides correctly matched with the nucleotides of the template. In other words, a 3'-5' exonuclease may excise the correctly matched nucleotides at a faster rate than the mismatched ones from the 3' terminus, or excise both the correctly matched and the mismatched nucleotides at the same rate. Consequently, even where the DNA polymerase has 3'-5' exonuclease activity, it does not perform any useful proof-reading function during DNA polymerization.

It is also known that a 3'-5' exonuclease activity associated with a DNA polymerase, in the presence of low concentrations of dNTPs, often counteracts the normal chain elongation process catalyzed by the polymerase, induces cyclic incorporation and degradation of nucleotides over the same segment of template, or even operates more efficiently than the polymerase activity per se, to the extent of causing degradation of the primer. Consequently, removal of the 3'-5' exonuclease activity along with the 5'-3' exonuclease activity from the native DNA polymerases by chemical means or by genetic engineering techniques has become a standard procedure in producing DNA polymerases for sequencing. This is a common strategy to preserve the essential properties of a DNA polymerase.

For example, among the major commercially available sequencing enzymes (other than the native Taq (*Thermus aguaticus*) DNA polymerase which lacks a 3'-5' exonuclease activity de novo) the 3'-5' exonuclease activity has been removed from the native T7 DNA polymerase, which lacks a 5'-3' exonuclease, either by a chemical reaction that oxidizes the amino acid residues essential for the exonuclease activity (Sequenase Version 1) or genetically by deleting 28 amino acids essential for the 3'-5' exonuclease activity (Sequenase 2).

Vent$_R$(exo$^{31}$) DNA polymerase, which is recommended as the preferred form of the Vent DNA polymerase for sequencing, also has its 3'-5' exonuclease activity removed by genetic modification. The native Vent DNA polymerase and the Klenow fragment isolated from the native *E. coli* DNA polymerase I possess a 3'-5' exonuclease; but these enzymes are no longer considered the enzymes of choice for DNA sequencing.

The currently known Bst DNA polymerase (e.g., produced by Bio-Rad Laboratories) isolated and purified from the cells of *Bacillus stearothermophilus* for DNA sequencing is free of 3'-5' exonuclease activity (5).

IsoTherm™ DNA Polymerase, a commercially available Bst DNA polymerase for DNA sequencing, marketed by Epicentre Technologies (1402 Emil Street, Madison, Wis. 53713), is also based on a Bst DNA polymerase whose 3'-5' exonuclease activity has been enzymatically removed (6).

Only the rBst DNA Polymerase produced from an overexpressing recombinant clone in *E. coli*, which is the product of the DNA pol I gene of *Bacillus stearothermophilus*, possesses a 3'-5' exonuclease activity in addition to a 5'-3' exonuclease activity. However, due to the existence of an undesirable 5'-3' exonuclease activity and a 3'-5' exonuclease activity of unknown characteristics, the latter product is not recommended by the company for DNA sequencing (6).

SUMMARY OF THE INVENTION

This invention addresses the above-described problems in the art by providing a novel DNA polymerase which is capable of proof-reading 3'-5' exonuclease activity. In this invention, the term "proof-reading" is intended to denote that the DNA polymerase is capable of removing mismatched nucleotides from the 3' terminus of a newly formed DNA strand at a faster rate than the rate at which nucleotides correctly matched with the nucleotides of the template are removed during DNA sequencing. In particular, the invention provides the DNA and amino acid sequences for the isolated and purified DNA polymerase having this function, as well as the DNA and amino acid sequences for the cloned and expressed DNA polymerase having this function.

The invention also provides a DNA construct comprising at least one of the above-described DNA sequences and a vector (such as a cloning vector or an expression vector), for introducing the DNA construct into eucaryotic or procaryotic host cells (such as an *E. coli* host cell). In addition, the invention further provides a host cell stably transformed with the DNA construct in a manner allowing production of the peptide encoded by the DNA segment in the construct.

The invention also provides improved methods for replicating DNA and sequencing DNA using the above-described DNA polymerases of the invention.

Preferably, the method of sequencing a DNA strand may comprise the steps of:

i) hybidizing a primer to a DNA template to be sequenced;
ii) extending the primer using a DNA polymerase which is capable of proofreading 3'-5' exonuclease activity, such that the DNA polymerase functions to excise mismatched nucleotides from the 3' terminus of the DNA strand at a faster rate than the rate at which the DNA polymerase functions to remove nucleotides matched correctly with nucleotides of the template, and which DNA polymerase does not exhibit 5'-3' exonuclease activity, in the presence of nucleotide bases dATP, dGTP, dCTP and dTTP, or their analogs, and ddNTP chain terminators; and
iii) allowing a DNA strand to be sequenced.

The invention also provides a test to screen for the DNA polymerase of the invention in different strains of bacteria, such as thermophilic organisms (i.e., *Bacillus stearothermophilus*), isolated from various sources.

Further objects and advantages of the invention will become apparent from the description and examples below.

DETAILED DESCRIPTION OF THE INVENTION

Figure 1:
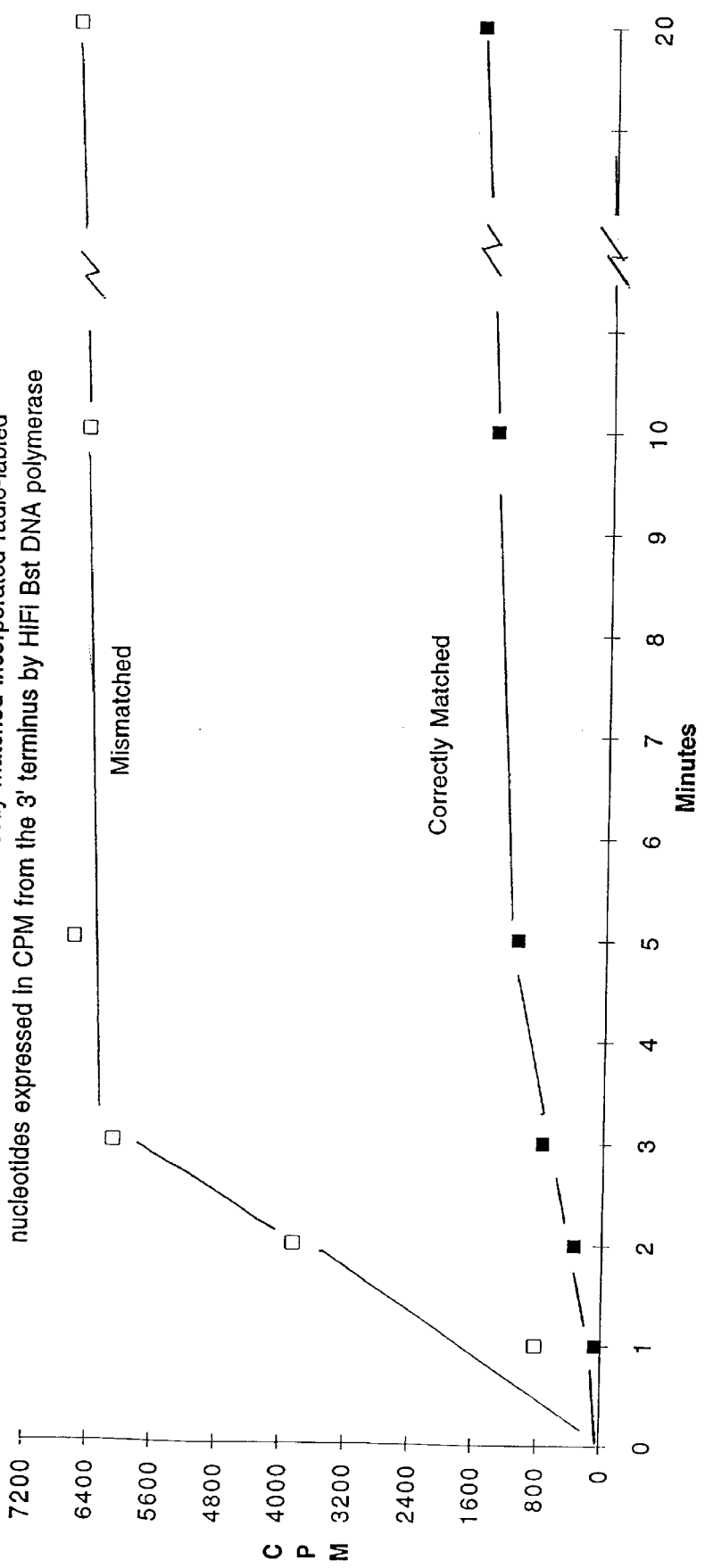
FIG. 1. This graph shows the excision of mismatched and correctly matched incorporated radio-labeled nucleotides expressed in CPM (counts per minute) from the 3' terminus by HiFi Bst DNA polymerase. (HiFi Bst DNA polymerase is described below.)

The DNA polymerases of the invention are capable of proofreading 3'-5' exonuclease activity, such that the DNA polymerases function to excise mismatched nucleotides from the 3' terminus of the DNA strand at a faster rate than the rate at which nucleotides matched correctly with nucleotides of the template are removed, and which DNA polymerases do not exhibit 5'-3' exonuclease activity.

In one embodiment, the invention entails a DNA sequence and an amino acid sequence for DNA polymerase such as the following:

DNA sequence:
GCCGAAGGGG AGAAACCGCT TGAGGAGATG GAGTTTGCCA

TCGTTGACGT CATTACCGAA GAGATGCTTG CCGACAAGGC

AGCGCTTGTC GTTGAGGTGA TGGAAGAAAA CTACCACGAT

GCCCCGATTG TCGGAATCGC ACTAGTGAAC GAGCATGGGC

GATTTTTTAT GCGCCCGGAG ACCGCGCTGG CTGATTCGCA

ATTTTTAGCA TGGCTTGCCG ATGAAACGAA GAAAAAAAGC

ATGTTTGACG CCAAGCGGGC AGTCGTTGCC TTAAAGTGGA

AAGGAATTGA GCTTCGCGGC GTCGCCTTTG ATTTATTGCT

DNA sequence:
CGCTGCCTAT TTGCTCAATC CGGCTCAAGA TGCCGGCGAT

ATCGCTGCGG TGGCGAAAAT GAAACAATAT GAAGCGGTGC

GGTCGGATGA AGCGGTCTAT GGCAAAGGCG TCAAGCGGTC

GCTGCCGGAC GAACAGACGC TTGCTGAGCA TCTCGTTCGC

AAAGCGGCAG CCATTTGGGC GCTTGAGCAG CCGTTTATGG

ACGATTTGCG GAACAACGAA CAAGATCAAT TATTAACGAA

GCTTGAGCAC GCGCTGGCGG CGATTTTGGC TGAAATGGAA

TTCACTGGGG TGAACGTGGA TACAAAGCGG CTTGAACAGA

TGGGTTCGGA GCTCGCCGAA CAACTGCGTG CCATCGAGCA

GCGCATTTAC GAGCTAGCCG GCCAAGAGTT CAACATTAAC

TCACCAAAAC AGCTCGGAGT CATTTTATTT GAAAAGCTGC

AGCTACCGGT GCTGAAGAAG ACGAAAACAG GCTATTCGAC

TTCGGCTGAT GTGCTTGAGA AGCTTGCGCC GCATCATGAA

ATCGTCGAAA ACATTTTGCA TTACCGCCAG CTTGGCAAAC

TGCAATCAAC GTATATTGAA GGATTGTTGA AAGTTGTGCG

CCCTGATACC GGCAAAGTGC ATACGATGTT CAACCAAGCG

CTGACGCAAA CTGGGCGGCT CAGCTCGGCC GAGCCGAACT

TGCAAAACAT TCCGATTCGG CTCGAAGAGG GGCGGAAAAT

CCGCCAAGCG TTCGTCCCGT CAGAGCCGGA CTGGCTCATT

TTCGCCGCCG ATTACTCACA AATTGAATTG CGCGTCCTCG

CCCATATCGC CGATGACGAC AATCTAATTG AAGCGTTCCA

ACGCGATTTG GATATTCACA CAAAAACGGC GATGGACATT

TTCCAGTTGA GCGAAGAGGA AGTCACGGCC AACATGCGCC

GCCAGGCAAA GGCCGTTAAC TTCGGTATCG TTTACGGAAT

TAGCGATTAC GGATTGGCGC AAAACTTGAA CATTACGCGC

AAAGAAGCTG CCGAATTTAT CGAACGTTAC TTCGCCAGCT

TTCCGGGCGT AAAGCAGTAT ATGGAAAACA TAGTGCAAGA

AGCGAAACAG AAAGGATATG TGACAACGCT GTTGCATCGG

-continued

DNA sequence:
CGCCGCTATT TGCCTGATAT TACAAGCCGC AATTTCAACG

TCCGCAGTTT TGCAGAGCGG ACGGCCATGA ACACGCCAAT

TCAAGGAAGC GCCGCTGACA TTATTAAAAA AGCGATGATT

GATTTAGCGG CACGGCTGAA AGAAGAGCAG CTTCAGGCTC

GTCTTTTGCT GCAAGTGCAT GACGAGCTCA TTTTGGAAGC

GCCAAAAGAG GAAATTGAGC GATTATGTGA GCTTGTTCCG

GAAGTGATGG AGCAGGCCGT TACGCTCCGC GTGCCGCTGA

AAGTCGACTA CCATTACGGC CCAACATGGT ATGATGCCAA

ATAA  (1764 nucleotides total)
(SEQ ID NO: 1)

The invention also includes any DNA sequence that is complementary thereto, for instance, DNA sequences that would hybridize to the above DNA sequence under stringent conditions.

(As would be apparent to someone skilled in this art, this DNA sequence does not indicate the starting codon.)

Amino acid sequence:
AEGEKPLEEM  EFAIVDVITE   EMLADKAALV  VEVMEENYHD

APIVGIALVN  EHGRFFMRPE   TALADSQFLA  WLADETKKKS

MFDAKRAVVA  LKWKGIELRG   VAFDLLLAAY  LLNPAQDAGD

IAAVAKMKQY  EAVRSDEAVY   GKGVKRSLPD  EQTLAEHLVR

KAAAIWALEQ  PFMDDLRNNE   QDQLLTKLEH  ALAAILAEME

FTGVNVDTKR  LEQMGSELAE   QLRAIEQRIY  ELAGQEFNIN

SPKQLGVILF  EKLQLPVLKK   TKTGYSTSAD  VLEKLAPHHE

IVENILHYRQ  LGKLQSTYIE   GLLKVVRPDT  GKVHTMFNQA

LTQTGRLSSA  EPNLQNIPIR   LEEGRKIRQA  FVPSEPDWLI

FAADYSQIEL  RVLAHIADDD   NLIEAFQRDL  DIHTKTAMDI

FQLSEEEVTA  NMRRQAKAVN  FGIVYGISDY  GLAQNLNITR

KEAAEFIERY  FASFPGVKQY   MENIVQEAKQ  KGYVTTLLHR

RRYLPDITSR  NFNVRSFAER   TAMNTPIQGS  AADIIKKAMI

DLAARLKEEQ  LQARLLLQVH   DELILEAPKE  EIERLCELVP

EVMEQAVTLR  VPLKVDYHYG   PTWYDAK (SEQ ID NO: 2)

Amino acid sequence:
where,

A: alanine (Ala)           M: methionine (Met)

C: cysteine (Cys)          N: asparagine (Asn)

D: aspartic acid (Asp)     P: proline (Pro)

E: glutamic acid (Glu)     Q: glutamine (Gln)

F: phenylanaline (Phe)     R: arginine (Arg)

G: glycine (Gly)           S: serine (Ser)

H: histidine (His)         T: threonine (Thr)

I: isoleucine (Ile)        V: valine (Val)

K: lycine (Lys)            W: tryptophan (Trp)

L: leucine (Leu)           Y: tyrosine (Tyr)

This DNA sequence and amino acid sequence obtainable by, for instance, isolating and purifying DNA polymerase from a thermostable *Bacillus stearothermophilus* (or from a bacterial strain otherwise derived from *Bacillus stearothermophilus* or other thermophilic strains) which is capable of producing a DNA polymerase which is capable of proofreading 3'-5' exonuclease activity, but does not exhibit 5'-3' exonuclease activity, as described above. As would be understood by someone skilled in the art, the invention also contemplates any DNA sequence that encodes a peptide having these characteristics and properties (including degenerate DNA code).

In another embodiment, the invention entails a DNA sequence and an amino acid sequence for DNA polymerase such as the following:

DNA sequence:
ATGGAA GCCAAAGGGG AGAAACCGCT TGAGGAGATG

GAGTTTGCCA TCGTTGACGT CATTACCGAA GAGATGCTTG

CCGACAAGGC AGCGCTTGTC GTTGAGGTGA TGGAAGAAAA

CTACCACGAT GCCCCGATTG TCGGAATCGC ACTAGTGAAC

GAGCATGGGC GATTTTTTAT GCGCCCGGAG ACCGCGCTGG

CTGATTCGCA ATTTTTAGCA TGGCTTGCCG ATGAAACGAA

GAAAAAAGC ATGTTTGACG CCAAGCGGGC AGTCGTTGCC

TTAAAGTGGA AAGGAATTGA GCTTCGCGGC GTCGCCTTTG

ATTTATTGCT CGCTGCCTAT TTGCTCAATC CGGCTCAAGA

DNA sequence:
TGCCGGCGAT ATCGCTGCGG TGGCGAAAAT GAAACAATAT

GAAGCGGTGC GGTCGGATGA AGCGGTCTAT GGCAAAGGCG

TCAAGCGGTC GCTGCCGGAC GAACAGACGC TTGCTGAGCA

TCTCGTTCGC AAAGCGGCAG CCATTTGGGC GCTTGAGCAG

CCGTTTATGG ACGATTTGCG GAACAACGAA CAAGATCAAT

TATTAACGAA GCTTGAGCAC GCGCTGGCGG CGATTTTGGC

TGAAATGGAA TTCACTGGGG TGAACGTGGA TACAAAGCGG

CTTGAACAGA TGGGTTCGGA GCTCGCCGAA CAACTGCGTG

CCATCGAGCA GCGCATTTAC GAGCTAGCCG GCCAAGAGTT

CAACATTAAC TCACCAAAAC AGCTCGGAGT CATTTTATTT

GAAAAGCTGC AGCTACCGGT GCTGAAGAAG ACGAAAACAG

GCTATTCGAC TTCGGCTGAT GTGCTTGAGA AGCTTGCGCC

GCATCATGAA ATCGTCGAAA ACATTTTGCA TTACCGCCAG

CTTGGCAAAC TGCAATCAAC GTATATTGAA GGATTGTTGA

AAGTTGTGCG CCCTGATACC GGCAAAGTGC ATACGATGTT

CAACCAAGCG CTGACGCAAA CTGGGCGGCT CAGCTCGGCC

GAGCCGAACT TGCAAAACAT TCCGATTCGG CTCGAAGAGG

GGCGGAAAAT CCGCCAAGCG TTCGTCCCGT CAGAGCCGGA

CTGGCTCATT TTCGCCGCCG ATTACTCACA AATTGAATTG

CGCGTCCTCG CCCATATCGC CGATGACGAC AATCTAATTG

AAGCGTTCCA ACGCGATTTG GATATTCACA CAAAAACGGC

GATGGACATT TTCCAGTTGA GCGAAGAGGA AGTCACGGCC

AACATGCGCC GCCAGGCAAA GGCCGTTAAC TTCGGTATCG

TTTACGGAAT TAGCGATTAC GGATTGGCGC AAAACTTGAA

CATTACGCGC AAAGAAGCTG CCGAATTTAT CGAACGTTAC

TTCGCCAGCT TTCCGGGCGT AAAGCAGTAT ATGGAAAACA

TAGTGCAAGA AGCGAAACAG AAAGGATATG TGACAACGCT

GTTGCATCGG CGCCGCTATT TGCCTGATAT TACAAGCCGC

AATTTCAACG TCCGCAGTTT TGCAGAGCGG ACGGCCATGA

ACACGCCAAT TCAAGGAAGC GCCGCTGACA TTATTAAAAA

AGCGATGATT GATTTAGCGG CACGGCTGAA AGAAGAGCAG

CTTCAGGCTC GTCTTTTGCT GCAAGTGCAT GACGAGCTCA

TTTTGGAAGC GCCAAAAGAG GAAATTGAGC GATTATGTGA

GCTTGTTCCG GAAGTGATGG AGCAGGCCGT TACGCTCCGC

GTGCCGCTGA AAGTCGACTA CCATTACGGC CCAACATGGT

ATGATGCCAA ATAA (1770 nucleotides total)

(SEQ ID NO: 3)

The invention also includes any DNA sequence that is complementary thereto, for instance, DNA sequences that would hybridize to the above DNA sequence under stringent conditions.

Amino acid sequence:
MEAKGEKPLE EMEFAIVDVI TEEMLADKAA LVVEVMEENY

HDAPIVGIAL VNEHGRFFMR PETALADSQF LAWLADETKK

KSMFDAKRAV VALKWKGIEL RGVAFDLLLA AYLLNPAQDA

GDIAAVAKMK QYEAVRSDEA VYGKGVKRSL PDEQTLAEHL

VRKAAAIWAL EQPFMDDLRN NEQDQLLTKL EHALAAILAE

MEFTGVNVDT KRLEQMGSEL AEQLRAIEQR IYELAGQEFN

INSPKQLGVI LFEKLQLPVL KKTKTGYSTS ADVLEKLAPH

HEIVENILHY RQLGKLQSTY IEGLLKVVRP DTGKVHTMFN

QALTQTGRLS SAEPNLQNIP IRLEEGRKIR QAFVPSEPDW

LIFAADYSQI ELRVLAHIAD DDNLIEAFQR DLDIHTKTAM

DIFQLSEEEV TANMRRQAKA VNFGIVYGIS DYGLAQNLNI

TRKEAAEFIE RYFASFPGVK QYMENIVQEA KQKGYVTTLL

HRRRYLPDIT SRNFNVRSFA ERTAMNTPIQ GSAADIIKKA

MIDLAARLKE EQLQARLLLQ VHDELILEAP KEEIERLCEL

VPEVMEQAVT LRVPLKVDYH YGPTWYDAK (SEQ ID NO: 4)

This DNA sequence and amino acid sequence may be obtained from, for instance, cloned and expressed DNA polymerase which is capable of proofreading 3'-5' exonuclease activity, but does not exhibit 5'-3' exonuclease activity, as described above. As would be understood by someone skilled in the art, this embodiment of the invention does not only contemplate DNA sequences and amino acid sequences cloned and expressed from *Bacillus stearothermophilus*, or otherwise derived from *Bacillus stearothermophilus*, but also contemplates any amino acid sequence that encodes a DNA polymerase capable of proof-reading 3'-5' exonuclease activity, such that the DNA polymerase functions to excise mismatched nucleotides from the 3' terminus of the DNA strand at a faster rate than the rate at which nucleotides matched correctly with nucleotides of the template are removed, and which DNA polymerase does not exhibit 5'-3' exonuclease activity, as described above. The invention also contemplates any DNA sequence that encodes a peptide having these characteristics and properties (including degenerate DNA code).

As can be seen from a comparison of the two DNA sequences described above, the first DNA sequence (obtainable by isolating and purifying the Bst DNA polymerase from a thermostable *Bacillus stearothermophilus*) does not include a starting codon, although a starting codon could easily be added without undue experimentation. However, the second DNA sequence (obtainable by cloning and expressing the Bst DNA polymerase from a thermostable *Bacillus stearothermophilus*) does include a starting codon. In addition, the second DNA sequence has nucleotide A (adenine) at position 10 (as opposed to nucleotide G (guanine) at position 4 in the first DNA sequence), which results in a higher expression of the DNA polymerase.

Both the purified and cloned DNA polymerases of the invention also contemplate allelic variations and mutations (for instance, adding or deleting nucleotides or amino acids, sequence recombination or replacement or alteration) which result in no change in the function of the above-described DNA polymerases or in their characteristics. For instance, the DNA polymerases encompass non-critical substitutions of nucleotides or amino acids that would not change functionality (i.e., such as those changes caused by a transformant host cell). In addition, the invention is intended to include fusion proteins and muteins of the unique DNA polymerases of the invention.

The invention also contemplates variations and mutations which give rise to a change in the function of the DNA polymerases or in their characteristics.

The invention also provides a DNA construct comprising at least one of the above-described DNA sequences and a vector (such as a cloning vector or an expression vector), for introducing the DNA construct into host cells. An example of a suitable vector is pYZ34/LF, described below.

The host cells need only be capable of being stably transformed with the DNA construct in a manner allowing production of the peptide encoded by the DNA segment in the construct (preferably in large quantity). The host cells may be of eucaryotic or procaryotic origin (such as a *E. coli* host cell). For instance, the host cell may be a thermophilic organism, although this is not a necessary requirement in order that a host cell be effective.

The invention also provides improved methods for replicating DNA using the above-described DNA polymerases. The methods entail replicating a DNA strand by conventional protocols with the modification of using a DNA polymerase described above, in the presence of nucleotides dATP, dGTP, dCTP and dTTP, or their analogs, and ddNTP chain terminators.

The invention also provides improved methods for DNA sequencing using the above-described DNA polymerases. The methods entail sequencing a DNA strand by conventional protocols with the following modifications:

i) hybidizing a primer to a DNA template to be sequenced;

ii) extending the primer using a DNA polymerase described above, in the presence of nucleotides dATP, dGTP, dCTP and dTTP, or their analogs, and ddNTP chain terminators; and iii) allowing a DNA strand to be sequenced.

In addition, the invention contemplates other uses of the DNA polymerase. For instance, the DNA polymerase can also be use in (1) filling-in 5' overhangs of DNA fragments; (2) synthesis of DNA probes by random primers labeling methodology; and (3) site-directed mutagenesis.

The DNA polymerases of the invention may be acquired using methods conventional in the art to screen and identify bacterial DNA polymerases with a proof-reading 3'-5' exonuclease activity for DNA sequencing. Preferably, the DNA polymerases of the invention are extracted from *Bacillus stearothermophilus*, or are otherwise derived from *Bacillus stearothermophilus* or other thermophilic organisms. For instance, the polymerase can be obtained by segregating strains of *Bacillus stearothermophilus* into different groups according to the proof-reading exonuclease activity of their respective DNA polymerases.

As someone skilled in the art would understand, the DNA polymerase of the invention could be obtained or produced by other strains of bacteria, especially thermophilic bacteria, besides *Bacillus stearothermophilus*. For instance, using the primers and methods of screening described herein, someone skilled in the art would isolate a DNA polymerase having the same properties and function from other strains.

As an example, the inventors have successfully purified from the cells of a strain of Bst (called Bst 320 for labeling purposes) a thermostable DNA polymerase from which the 5'-3' exonuclease activity was removed by digestion with subtilisin. The resultant enzyme possessed a proof-reading 3'-5' exonuclease activity which removed mismatched nucleotides from an elongating DNA strand at a higher rate than those correctly matched with the template. This new enzyme is distinguishable from Bst DNA polymerase previously known in the art which does not have a 3'-5' exonuclease activity. Bst 320 was deposited on Oct. 30, 1995 in the American Type Culture Collection, located at 12301 Parklawn Drive, Rockville, Md. 20852, and has been given ATCC Designation No. 55719.

Similar to the previously known Bst DNA polymerase which has been well characterized by one of the inventors (4), the DNA polymerases of the invention (large fragment) have an apparent molecular weight of about 75,000 daltons, and have no 5'-3' exonuclease activity. The polymerases of the invention are functional in temperatures between 25° C. and 75° C., and are most active at 65° C. Thus, these polymerases are capable of overcoming the hindrance of secondary structures along the single-stranded DNA templates in DNA sequencing.

All four dNTPs, including dCTP, are incorporated equally effectively in the chain elongation during sequencing reaction catalyzed by the DNA polymerases of the invention with a high processivity and a high elongating rate. There is no "weak C band" phenomenon often observed when other DNA polymerases are used. In addition, the enzyme can incorporate nucleotide analogs, such as ddNTPs, dITP and 7-deaza-dGTP without undue discrimination, and it produces a very good band uniformity in the sequencing gel.

The DNA polymerases of the invention can be used both in the classic Sanger one-step reaction as well as in the "labeling/termination" sequencing reaction, double-stranded DNA sequencing, and the incorporation of $^{35}$S-labeled nucleotides, and $^{32}$P-labeled nucleotides. Since the enzyme can be stored at room temperature for at least two weeks without significant loss of its enzymatic activity, it can be adapted for robotic automation of DNA sequencing which requires a stable DNA polymerase, using either fluorescent dye or radioactive isotope labeling.

This invention also involves a method to measure the proof-reading 3'-5= exonuclease activity of purified DNA polymerases. The method is useful to screen a large number of bacterial strains, such as *Bacillus stearothermophilus* and other thermophilic bacterial strains, to select a strain which produces a DNA polymerase with a high proof-reading 3'-5' exonuclease activity. For instance, the method to test the proof-reading 3'-5' exonuclease activity of DNA polymerase was carried out as follows.

A DNA primer and two DNA templates with following sequences were synthesized chemically, using a DNA synthesizer.

17-base primer 5' CATTTTGCTGCCGGTCA 3'
                  1 mg/ml
                 (SEQ ID NO: 5)

Template (a) 3'------GTAAAACGACGGCCAGTCTT------5'
                           10 mg/ml
                        (SEQ ID NO: 6)

Template (b) 3'------GTAAAACGACGGCCAGTCTT------5'
                           10 mg/ml
                        (SEQ ID NO: 7)

To produce the radiolabeled primer, 1 µl (1 µg) of primer, 5 µl (50 µg) of template (a), 1 µl of [α-$^{32}$P] dATP (800 Ci/mmole), 1 µl of dGTP (0.5 mM), 1 µl of Taq DNA polymerase (1 unit), and 1 µl of buffer consisting of 500 mM Tris-Cl, pH 9.0, and 150 mM MgCl$_2$, were mixed in a test tube and incubated in a 65° C. water bath for 5 minutes. The mixture was subject to alkaline denaturing gel electrophoresis. The radioactive band containing the 20-base nucleotide was isolated and dissolved in 12 µl of 10 mM Tris-Cl buffer, containing 1 mM EDTA, pH 8.0. The final product represents the following labeled 20-base primer.

5' CATTTTGCTGCCGGTCAGA*A*   3'
         (* = $^{32}$P labeled)
         (SEQ ID NO: 8)

To produce radiolabeled primer-template complexes, 5 µl of the labeled primer was mixed with 10 µl of template (a) or template (b) respectively to form the following:

Complex (a)
5'CATTTTGCTGCCGGTCAGA*A* 3'  (same as SEQ ID NO: 8)
3'GTAAAACGACGGCCAGTCT  T  5'  (same as SEQ ID NO: 6)

Complex (b)
5'CATTTTGCTGCCGGTCAGA*A* 3'  (same as SEQ ID NO: 8)
3'GTAAAACGACGGCCAGTCG  G  5'  (same as SEQ ID NO: 7)

The free radiolabeled primer was removed through a G-50 Sephadex column.

An aliquot of complex (a) which had two correctly matched radiolabeled A*s at the 3' terminus of the primer, and an aliquot of complex (b) which had two mismatched A*s at the 3' terminus of the primer, were then pipetted into two individual vials of scintillation fluid and their radioactivity was measured in a scintillation counter, and both complexes were adjusted with buffer to a concentration containing the same molarity of incorporated [α$^{32}$P] dAMP.

To perform the proof-reading 3'-5' exonuclease activity, 20 µl of complex (a) or complex (b), 8 µl reaction buffer consisting of 15 mM Tris-Cl and 15 MM MgCl$_2$, pH 8.5, 4 units of DNA polymerase, and enough water to make up a total volume of 40 µl were pipetted into a test tube and mixed well. The mixture was subdivided into aliquots of 3 µl each in 0.5 ml microcentrifuge tubes and was then covered with 3 µl paraffin in each tube. The microcentrifuge tubes were incubated in a 65° C. water bath. At 1, 2, 3, 5, 10, and 20 minutes, a pair of the microcentrifuge tubes were taken out from the water bath and the content of each tube was dotted onto a DE-81 Whatman filter paper. One of each pair of the filter papers was put in scintillation fluid directly and the radioactivity was counted in cpm value in a scintillation counter; the other was washed three times in 0.3 M sodium phosphate buffer, pH 6.8 before being put into the scintillation fluid for counting.

The difference in radioactivity expressed in cpm value between the washed filter paper and the unwashed filter paper in each pair was interpreted as representing the relative quantity of labeled nucleotides excised by the 3'-5' exonuclease activity from the 3' terminus of the primer. A DNA polymerase that excised the radiolabeled nucleotides A*s from complex (b) more efficiently than from complex (a) possessed proof-reading 3'-5' exonuclease activity. A DNA polymerase that excised the radiolabeled nucleotides A*s from complex (a) faster than from complex (b), or at nearly the same rate, was interpreted as possessing a non-specific 3'-5' exonuclease activity which is considered unsuitable for DNA sequencing.

Using these methods, a strain of bacteria was isolated from among the strains of *Bacillus stearothermophilus* from various sources which is distinguished in its fast growth rate. This strain reached an optimum exponential growth within 3 hours for DNA polymerase production. The strain is also novel in its ability to produce a DNA polymerase with a proof-reading 3'-5' exonuclease activity. This strain of *Bacillus stearothermophilus* was labeled Bst No. 320.

As persons skilled in this art would appreciate, the bacterial strain, or even the strain of *Bacillus stearothermophilus*, from which the thermostable DNA polymerase of the invention can be obtained is not limited to Bst No. 320. On the contrary, the polymerase may be derived using the above-described methods or others known in the art from strains of *Bacillus stearothermophilus* or other bacteria strains (especially thermophilic strains), including wild strains or mutant strains acquired by various means, including spontaneous mutation.

To prepare the preferred purified Bst DNA polymerase of the invention, the cells of Bst No. 320 were grown at 55° C. in a liquid medium consisting of 1% polypeptone, 0.5% yeast extract and 0.5% NaCl, pH7.0–7.2. The 3 hr old cells were collected after centrifugation and suspended in 4 volumes of TME buffer (50 mM Tris-HCl, pH7.5, 10 mM β-mercaptoethanol, and 2 mM EDTA), containing 100 mg lysozyme and 23 mg phenylmethylsulphonyl-fluoride/ml. The cells were broken by sonication in ice. The supernatant was pooled after centrifugation at 28,000 rpm in a Spinco L 30 rotor.

The purified Bst DNA polymerase of the invention was prepared according to Okazaki and Kornberg (7) with appropriate slight modifications and the large fragment of the DNA polymerase was obtained by partial digestion of the whole DNA polymerase with the proteinase subtilisin (type Carlsberg) basically according to Jacobsen et al. (8).

The procedure for purification of enzyme was followed as described in Ye and Hong (4). This Bst DNA polymerase possessed a proof-reading 3'-5' exonuclease activity. For identification purposes, it was labeled by the inventors as HiFi Bst.

The HiFi Bst was tested for proof-reading and non-specific 3'-5' exonuclease activities as described above. The results showed that the HiFi Bst excised the mismatched incorporated nucleotides from the 3' terminus of a double-stranded DNA at a high rate, reaching the plateau of hydrolysis in about 3 minutes, about 8 times more efficiently in the first 3 minutes of reaction than those correctly matched with the nucleotides of the template (FIG. 1).

The following non-limiting examples are illustrative of the invention.

The Isolation of the DNA Sequence Which Contained the Gene for DNA Polymerase of the Invention 1. Partial amino acid sequencing of the holoenzyme DNA polymerase and Bst DNA polymerase of the invention:

The holoenzyme DNA polymerase (Bst-holo) was purified from *Bacillus stearothermophilus* strain Bst No.320. The Bst DNA polymerase was prepared from Bst-holo according to the procedures described above. The N termini of purified Bst-holo and Bst DNA polymerase were determined by using an Applied Biosystems 477A Protein Sequencer. The N terminal sequences obtained were as follows:

The N terminal amino acid sequence of Bst-holo:

MetLysLysLysLeuValLeuIleAspGlyAsnSerValAlaTyr (SEQ ID NO:9)

The N terminal amino acid sequence of Bst DNA polymerase:

GluLysProLeuLeuGluMetArgPheCysIleValAsp (SEQ ID NO:10)

2. The 5' DNA sequence of the gene for Bst-holo obtained by polymerase chain reaction (PCR):

The degenerate pools of 5' forward primer and 3' reverse primer were synthesized according to the N terminal amino acid sequences of Bst-holo and Bst DNA polymerase respectively. They were as follows:

5'-(+) primer:

5'- ATCTCGGATCCATGAAAAAAAAACTAGTGCTAATCGG
       Bam HI                  T G  CT G   T

NAATTCCGTCGC   (SEQ ID NO: 11)
  CAG    G

3'-(−) primer:

5'-
ATAGAGTCGACAATGCAGAAGCGCATTTCTAGTAGGGGTTTTTC
       Sal  I   G        A   C          C AC A       C

The template was the chromosome DNA purified from *Bacillus Stearothermophilus* strain Bst No.320.

The reaction system

| | |
|---|---|
| 50 mM | KCl |
| 10 mM | Tris-HCl |
| | (pH = 9.0 at room temp.) |
| 2.5 mM | MgCl$_2$ |
| 0.01% (w/v) | Gelatin |
| 0.01% (w/v) | Triton X-100 |
| 50 μM | dNTP each |
| 10 ng | Chromosome DNA |
| 50 pmol | primer each |
| 2 u | Taq DNA polymerase |
| Total Volume = 100 μl | |

The reaction procedure:

94° C. denaturation for 5 minutes
a. 94° C. denaturation for 30 seconds
b. 37° C. anealing for 2 minutes
c. 72° C. polymerization for 3 minutes a–c five cycles;
d. 94° C. denaturation for 30 seconds
e. 46° C. anealing for 1 minutes
f. 72° C. polymerization for 2 minutes d–f 25 cycles;
72° C. elongation for 5 minutes.

The reaction mixture was purified and analysed by 1% agarose gel electrophoresis. The products were of about 1.0 Kb in length, which was in agreement with the size of small fragment of Bst-holo. The purified products were digested by Bam HI and Sal I, followed by cloning into pUC19 plasmid, which was predigested by the same restriction enzymes. The recombinant plasmid thus obtained was transformed into *E. coli* TG1.

3. Obtaining the DNA sequence containing the gene for DNA polymerase of the invention:

The segment of the 5' sequence of the gene for Bst-holo prepared in procedure 2 was used to produce a probe for isolation of the DNA sequences which contained the entire gene for the Bst DNA polymerase of the invention. The cloned recombinant plasmid DNA obtained in procedure 2 was initially digested with a mixture of Sal I and Dra I. The digested DNA fragments were purified by 8% agarose gel electrophoresis, and a DNA segment of about 100 bp in length was selected and labelled with radioactive isotope by random primer labelling. This labelled 100 bp fragment was used as the probe.

The chromosome DNA of *Bacillus stearothermophilus* was digested by Cla I, Pvu II and Dra I individually to completion, and the digests were subject to electrophoresis on 0.7% agarose gel. Using Southern blotting, the DNA on the gel stained with ethidium bromide was transferred onto Hybond N$^+$ membrane by VacuGene™ XL (Pharmacia), and was hybridized with the labelled radioactive probe.

According to the results of the Southern blotting, a band of DNA fragments of about 2.5 Kb in length produced by digestion with Cla I was found to hybridize with the radioactive probe. This band was ligated into pUC18 plasmid which plasmid had been predigested with Acc I and dephosphorylated by alkaline phosphatase (CIP). The recombinant plasmids thus obtained were named pUC18/LF and were then transformed into *E. coli* TG1. The candidate clones of the transformed *E. coli* containing the pUC18/LF plasmid were screened out by hybridization with the radioactive probe described above.

The DNA sequence cloned in the plasmid pUC18/LF was determined by Sanger's sequencing method with progressive oligonucleotide primers. It was finally determined that within the 2.5 kb fragment inserted in the pUC18/LF plasmid, there lies the entire sequence for the Bst DNA polymerase of the invention. The total determined sequence was 2,363 bp in length, and the gene for the Bst DNA sequence was 1,764 bp in length.

The Isolation of the Cloned Gene for DNA polymerase of the Invention

To isolate the gene for DNA polymerase, two oligonucleotide primers were synthesized according to the known DNA sequences derived from both N & C termini of Bst DNA polymerase. Restriction enzyme sites were introduced into the two primers for the purpose of subsequent gene cloning and expression. The starting codon ATG for translation was also introduced into the 5' forward primer. The sequences of the two primers thus designed were as follows:

5'-(+)-primer: (SEQ ID NO: 13) 5'-AAA<u>CCATGGAATTC</u>ATGGAAGCCAAAGGGGAGAAACCGCTTGAGGAG
　　　　　　　　　　　　　　　　　　　NcoI　　Eco RI 3'-(−)-primer: (SEQ ID NO: 14) 5'-AAA<u>GGATCCTCTAGA</u>ATTGGCCGGCCCGTTTCCG
　　　　　　　　　　　　　　　　　　　Bam HI　Xba I The reaction system:

| | |
|---|---|
| 50 mM | KCl |
| 10 mM | Tris-HCl |
| | (pH = 9.0 at room temp.) |
| 1 mM | MgCl$_2$ |
| 0.01% (w/v) | Gelatin |
| 0.01% (w/v) | Triton X-100 |
| 50 μM | dNTP each |
| 100 ng | pUC18/LF as template |
| 100 pmol | primer each |
| 2 u | Taq DNA polymerase |
| | Total Volume = 100 μl |

The reaction procedure:
94° C. denaturation for 2 minutes
a. 94° C. denaturation for 30 seconds
b. 50° C. anealing for 30 seconds
c. 72° C. polymerization for 1.5 minutes a–c 30 cycles
72° C. elongation for 5 minutes.

The reaction product which contains the gene for the DNA polymerase of the invention thus obtained was purified by 1% agarose gel electrophoresis.

The gene for the DNA polymerase and the expression vector pYZ23 containing a strong λP$_L$ promoter were digested by both Eco RI and Bam HI, and the digests were purified and recovered from 1% low melting agarose gel after electrophoresis. The digested DNA and vector were ligated to form recombinant plasmid pYZ23/LF, which was then transformed into E. coli JF1125. The desired clone was further confirmed by restriction enzyme digestion analysis.

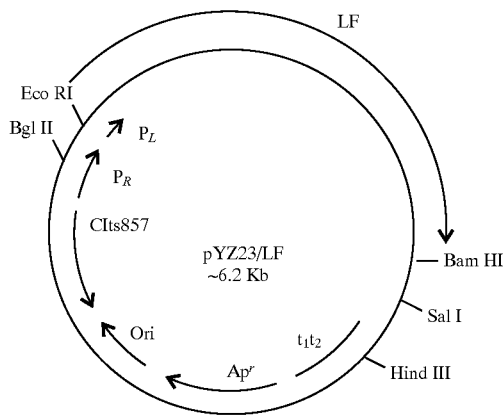

The Expression of the Cloned Gene for DNA Polymerase of the Invention

The E. coli JF1125 containing pYZ23/LF was inoculated into LB media culture containing 100 μg/ml ampicillin, and was incubated overnight at 30° C. The overnight culture was inoculated into large volume of fresh culture, and was incubated at 30° C. until the OD$_{600}$ of the culture reached 0.7. The culture was then heated at 41° C. and incubated for 3 hours for induction. The SDS-PAGE analysis of the cell extract showed that the amount of expressed Bst DNA polymerase constitute about 45.8% of the total soluble proteins of the cell. Therefore, it was confirmed that the cloned gene for DNA polymerase of the invention can be overexpressed.

Purification of the Product of the Cloned Gene for DNA Polymerase of the Invention 2 liter culture of E. coli containing pYZ23/LF grown in condition as described above were centrifuged at 5,000 rpm at 40° C. for 20 minutes. The pellets were suspended and washed with buffer [10 mM Tris-HCl ( pH7.5 at room temperature ), 10 mM β-Mercaptoethanol, 2 mM EDTA, 0.9% NaCl ], and recentrifuged. The pellets (about 8.68 g) were then suspended in 35 ml buffer [50 mM Tris-HCl ( pH7.5 at room temperature ), 10 mM β-Mercaptoethanol, 2 mM EDTA, 100 μg/ml Lysozyme, 23 μg/ml PMSF ], and sonicated on Sonicator W-375 ( Heat System Ultrasonics, Inc.). The cell extract was obtained by centrifugation at 18,000 rpm at 4° C. for 20 minutes, and then treated step by step as follows:

(A) The cell extract was heated at 60° C. for 30 minutes, and cooled to 4° C., then centrifuged at 15,000 rpm at 4° C. for 20 minutes;

(B) 5% Polymin P was added into supernatant to 0.6%, and mixed quickly for 30 minutes, then centrifuged at 15,000 rpm at 4° C. for 20 minutes;

(C) The pellet was resuspended in 30 ml buffer [50 mM Tris-HCl ( pH7.5 at room temperature ), 1 mM EDTA, 1 mM β-Mercaptoethanol, 800 mM NaCl, 5% Glycerol ] at 4° C., and then centrifuged at 15,000 rpm at 4° C. for 20 minutes;

(D) Ammonium sulfate was added into the supernatant to 60% saturation at 4° C., and mixed for 30 minutes, then centrifuged at 15,000 rpm at 4° C. for 20 minutes;

(E) The ammonium sulfate pellet was resuspended in 30 ml of 60% saturated ammonium sulfate at 4° C., and then recentrifuged at 15,000 rpm at 4° C. for 20 minutes;

(F) The pellet was suspended in 15 ml buffer [50 mM Tris-HCl ( pH7.5 at room temperature ), 1 mM EDTA, 1 mM β-Mercaptoethanol, 5% Glycerol ] and dialysed against the same buffer for hours, then centrifuged at 15,000 rpm at 4° C. for 20 minutes. The insoluble protein was discarded;

(G) The solution obtained was concentrated in Centricon 30 to minimal volume, glycerol was added to 50%.

The resulting DNA polymerase has been proven to be homogenous by polyacrylamide gel electrophoresis. The solution containing the expressed DNA polymerase was stored at −20° C.

Experiments showed that the cloned and expressed DNA polymerase of the invention possessed all the characteristics of the Bst DNA polymerase purified from Bst 320 cells.

Example of Using the Cloned and Expressed DNA Polymerase of the Invention for DNA Sequencing The following example is based on the standard Sanger protocol for single-strand DNA sequencing, using the DNA polymerase of the invention as the enzyme.

1. Into a 1.5 ml centrifuge tube, were pipetted the following: 1.0 μl of universal DNA sequence primer containing 2.5–5 ng DNA with the sequence of 5'-GTAAAACGACGGCCAGT-3' (SEQ ID NO:15), 7.0 μl of ssDNA template containing 250–500 ng DNA, and 2.0 μl of 5× reaction buffer consisting of 100 mM Tris-Cl, pH 8.5, and 100 mM MgCl$_2$.

2. The mixture was placed in a 75° C. water bath for 5 minutes, and then allowed to cool slowly to ambient temperature over the course of 5 minutes.

3. Into the tube, were added 1.5 μl [α-$^{35}$S] dATP (1000 Ci/mmole) and 1.0 μl of the Bst DNA polymerase of the invention containing 1.0 unit of the enzyme in 20 mM KH$_2$PO$_4$, pH 6.8, 10 mM β-mercaptoethanol, 50% glycerol. The contents were mixed and microcentrifuged for 2–3 seconds.

4. An aliquot of 2.5 μl of the mixture was pipetted into each of four tubes containing 2.0 μl of one of the following mix solution, pre-warmed to 65° C.:

A. 620 nM dATP, 62 μM dCTP, 62 μM dGTP, 62 μM dTTP, 25 μM ddATP in 1.5 mM Tris-Cl, 0.15 mM EDTA, pH 8.0

C. 800 nM dATP, 8 μM dCTP, 80 μM dGTP, 80 μM dTTP, 50 μM ddCTP in 1.5 mM Tris-Cl, 0.15 mM EDTA, pH 8.0

G. 800 nM dATP, 80 μM dCTP, 4 μM dGTP, 80 μM dTTP, 75 μM ddGTP in 1.5 mM Tris-Cl, 0.15 mM EDTA, pH 8.0

T. 800 nM dATP, 80 μM dCTP, 80 μM dGTP, 8 μM dTTP, 150 μM ddTTP in 1.5 mM Tris-Cl, 0.15 mM EDTA, pH 8.0

5. After mixing and microcentrifugation for 2–3 seconds, all four tubes, labeled A, C, G, and T, respectively, were placed in a 65° C. water bath for 2 minutes (elongation-termination reaction).

6. Into each of the four tubes, 2 μl of chase solution containing 0.5 mM for each of the four dNTPs (dATP, dCTP, dGTP and dTTP) dissolved in water was added. After mixing, the tubes were microcentrifuged and placed in a 65° C. water bath for further incubation for 2 minutes.

7. The reaction in all four tubes was stopped by adding 4 μl of stop solution consisting of 95% deionized formamide, 10 mM EDTA, 0.05% xylene cyanole FF, and 0.05% bromophenol blue. The mixture was microcentrifuged, and loaded in denaturing high resolution polyacrylamide gel for electrophoresis.

Figure 2:
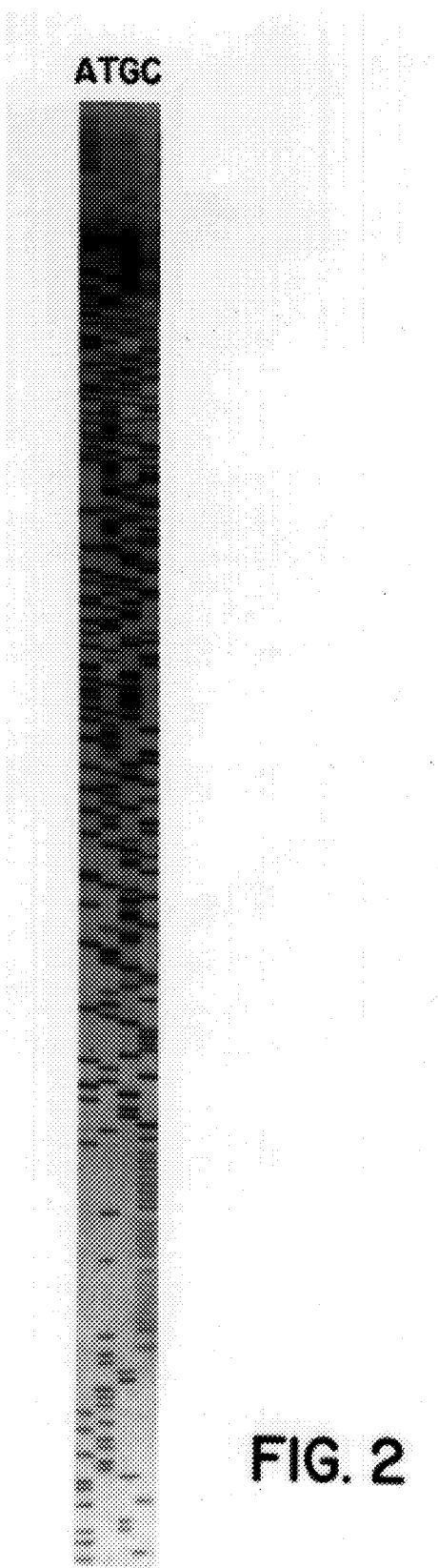
FIG. 2. This is a radioautograph of a sequencing gel obtained by using the DNA polymerase of the invention. A sequence pattern with discrete and evenly labeled bands can be clearly seen.

8. An autoradiographic image of the sequencing gel obtained (FIG. 2).

In further tests of the DNA polymerase of the invention, it has been demonstrated that the rate of mismatched base pair incorporation during DNA polymerization catalyzed by the enzyme was in the order of 7.8×10$^{-7}$. This is almost a 20-fold improvement in accuracy over the previously known Bst DNA polymerase, which has an error rate of approximately 1.5×10$^{-5}$ during DNA sequencing.

In addition, the DNA polymerase of the invention retains all other advantageous properties of the known Bst DNA polymerase. It also is functional within the temperature range between 25° C. and 75° C., and is most active at 65° C. All four dNTPs, including dCTP, and other nucleotide analogs, such as dITP and 7-deaza-dGTP, are incorporated equally effectively in the chain elongation (thus eliminating the weak "C" band phenomena) with an excellent band uniformity on the sequencing gel (FIG. 2).

The polymerase of the invention can be used both for the classic Sanger one-step reaction as well as for the "labeling/termination" sequencing reaction, double-stranded DNA sequencing, and the incorporation of $^{35}$S-labeled nucleotides, and $^{32}$P-labeled nucleotides (9). It can be used for rapid sequence analysis using nanogram amounts of template (10), and for automation of DNA sequencing which requires a stable DNA polymerase (11), using either fluorescent dye or radioactive isotope labeling (12).

All references mentioned herein are incorporated in their entirety by reference.

REFERENCES

1. Sanger, F., Nicklen, S. & Coulson, A. R. Proc. Nat. Acad.Sci., USA 74: 5463–5467. 1977.
2. CURRENT PROTOCOLS IN MOLECULAR BIOLOGY, Ausubel, F. M. et. Al. (Editors) Vol. I., John Wiley & Sons, Inc. 1995. pp 7.4.17–7.4.24.
3. Ibid p. 7.4.31.
4. Ye, S. Y. & Hong, G. F., Scientia Sinica (Series B) 30: 503–506. 1987.
5. In Ref. 2, p. 7.4.18 Table 7.4.2.
6. EPICENTRE TECHNOLOGIES CATALOG,1994/95 Products for Molecular & Cellular Biology, Page 1, "What's new in this catalog?"
7. Okazaki, T. & Kornberg, A. J. Biol. Chem. 239: 259–268. 1964.
8. Jacobsen, H., Klenow, H. & Overgard-Hansen, K. Eur. J. Biochem. 45: 623–627. 1974.
9. McClary, J., Ye, s. Y., Hong, G. F. & Witney, F. DNA Sequence 1: 173–180. 1991.
10. Mead, D. A., McClary, J. A., Luckey, J. A., et Al. BioTechniques 11: 76–87. 1991.
11. Earley, J. J., Kuivaniemi, H. Prockop, D. J. & Tromp, G. BioTechniques 17: 156–165,1994.
12. Mardis, E. R. & Bruce, A. R. BioTechniques 7: 840–850. 1989.

What is claimed is:

1. An isolated strain of *Bacillus stearothermophilus* which produces a peptide having SEQ ID NO:2.

2. The isolated strain of *Bacillus stearothermophilus* of claim 1, wherein the peptide is a thermostable DNA polymerase which proofreads 3'-5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

3. The isolated strain of *Bacillus stearothermophilus* of claim 1 which is Bst 320.

4. The isolated strain of *Bacillus stearothermophilus* of claim 1 wherein the peptide is encoded by a DNA segment having SEQ ID NO:1.

5. An isolated DNA segment having SEQ ID NO:1.

6. The purified peptide encoded by the DNA segment of claim 5.

7. A transformed host cell which produces a peptide having SEQ ID NO:4.

8. The transformed host cell of claim 7 wherein the peptide is a thermostable DNA polymerase which proofreads 3'-5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

9. The transformed host cell of claim 7 which is *E. coli*.

10. The transformed host cell of claim 9 which is *E. coli* JF1125.

11. The transformed host cell of claim 7 wherein the peptide is encoded by a DNA segment having SEQ ID NO:3.

12. An isolated DNA segment having nucleotide SEQ ID NO:3.

13. The purified peptide encoded by the DNA segment of claim 12.

14. A DNA construct comprising:
   (i) the DNA segment of claim 12; and
   (ii) a vector, for introducing the DNA construct into eucaryotic or procaryotic host cells.

15. The DNA construct of claim 14 wherein the vector is a cloning vector or an expression vector.

16. A host cell stably transformed with the DNA construct of claim 14 wherein expression of the peptide encoded by the DNA segment in the construct is achieved.

17. The host cell of claim 16, wherein the peptide is a thermostable DNA polymerase which proofreads 3'-5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

18. A DNA construct comprising:
   (i) the DNA segment encoding the peptide of claim 13; and
   (ii) a vector, for introducing the DNA construct into eucaryotic or procaryotic host cells.

19. The DNA construct of claim 18 wherein the vector is a cloning vector or an expression vector.

20. A host cell stably transformed with the DNA construct of claim 18 in a manner allowing expression of the peptide encoded by the DNA segment in the construct.

21. The purified thermostable DNA polymerase produced by the isolated strain of *Bacillus stearothermophilus* of claim 1, or produced by the transformed host cell of claim 7.

22. A method of replicating a DNA strand comprising the step of replicating a DNA strand using a DNA polymerase which proofreads 3'-5' exonuclease activity, such that the DNA polymerase functions to excise mismatched nucleotides from the 3' terminus of the polymerase functions to remove nucleotides matched correctly with nucleotides of the template;
   wherein the DNA polymerase has amino acid SEQ ID NO:2 or SEQ ID NO:4.

23. A method of sequencing a DNA strand comprising the steps of:
   i) hybridizing a primer to a DNA template to be sequenced;
   ii) extending the primer using a DNA polymerase which proofreads 3'-5' exonuclease activity, such that the DNA polymerase functions to excise mismatched nucleotides from the 3' terminus of the DNA strand at a faster rate than the rate at which the DNA polymerase functions to remove nucleotides matched correctly with nucleotides of the template, under such conditions that the DNA strand is sequenced;
   wherein the DNA polymerase has amino acid SEQ ID NO:2 or SEQ ID NO:4.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
　　　　　( A ) LENGTH: 1764 base pairs
　　　　　( B ) TYPE: nucleic acid
　　　　　( C ) STRANDEDNESS: single
　　　　　( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GCCGAAGGGG | AGAAACCGCT | TGAGGAGATG | GAGTTTGCCA | TCGTTGACGT | CATTACCGAA | 60 |
| GAGATGCTTG | CCGACAAGGC | AGCGCTTGTC | GTTGAGGTGA | TGGAAGAAAA | CTACCACGAT | 120 |
| GCCCCGATTG | TCGGAATCGC | ACTAGTGAAC | GAGCATGGGC | GATTTTTTAT | GCGCCCGGAG | 180 |
| ACCGCGCTGG | CTGATTCGCA | ATTTTTAGCA | TGGCTTGCCG | ATGAAACGAA | GAAAAAAAGC | 240 |
| ATGTTTGACG | CCAAGCGGGC | AGTCGTTGCC | TTAAAGTGGA | AAGGAATTGA | GCTTCGCGGC | 300 |
| GTCGCCTTTG | ATTTATTGCT | CGCTGCCTAT | TTGCTCAATC | CGGCTCAAGA | TGCCGGCGAT | 360 |
| ATCGCTGCGG | TGGCGAAAAT | GAAACAATAT | GAAGCGGTGC | GGTCGGATGA | AGCGGTCTAT | 420 |
| GGCAAAGGCG | TCAAGCGGTC | GCTGCCGGAC | GAACAGACGC | TTGCTGAGCA | TCTCGTTCGC | 480 |
| AAAGCGGCAG | CCATTTGGGC | GCTTGAGCAG | CCGTTTATGG | ACGATTTGCG | GAACAACGAA | 540 |
| CAAGATCAAT | TATTAACGAA | GCTTGAGCAC | GCGCTGGCGG | CGATTTTGGC | TGAAATGGAA | 600 |
| TTCACTGGGG | TGAACGTGGA | TACAAAGCGG | CTTGAACAGA | TGGGTTCGGA | GCTCGCCGAA | 660 |
| CAACTGCGTG | CCATCGAGCA | GCGCATTTAC | GAGCTAGCCG | GCCAAGAGTT | CAACATTAAC | 720 |
| TCACCAAAAC | AGCTCGGAGT | CATTTTATTT | GAAAAGCTGC | AGCTACCGGT | GCTGAAGAAG | 780 |
| ACGAAAACAG | GCTATTCGAC | TTCGGCTGAT | GTGCTTGAGA | AGCTTGCGCC | GCATCATGAA | 840 |
| ATCGTCGAAA | ACATTTTGCA | TTACCGCCAG | CTTGGCAAAC | TGCAATCAAC | GTATATTGAA | 900 |
| GGATTGTTGA | AAGTTGTGCG | CCCTGATACC | GGCAAAGTGC | ATACGATGTT | CAACCAAGCG | 960 |
| CTGACGCAAA | CTGGGCGGCT | CAGCTCGGCC | GAGCCGAACT | TGCAAAACAT | TCCGATTCGG | 1020 |
| CTCGAAGAGG | GGCGGAAAAT | CCGCCAAGCG | TTCGTCCCGT | CAGAGCCGGA | CTGGCTCATT | 1080 |
| TTCGCCGCCG | ATTACTCACA | AATTGAATTG | CGCGTCCTCG | CCCATATCGC | CGATGACGAC | 1140 |
| AATCTAATTG | AAGCGTTCCA | ACGCGATTTG | GATATTCACA | CAAAAACGGC | GATGGACATT | 1200 |
| TTCCAGTTGA | GCGAAGAGGA | AGTCACGGCC | AACATGCGCC | GCCAGGCAAA | GGCCGTTAAC | 1260 |
| TTCGGTATCG | TTTACGGAAT | TAGCGATTAC | GGATTGGCGC | AAAACTTGAA | CATTACGCGC | 1320 |
| AAAGAAGCTG | CCGAATTTAT | CGAACGTTAC | TTCGCCAGCT | TTCCGGGCGT | AAAGCAGTAT | 1380 |
| ATGGAAAACA | TAGTGCAAGA | AGCGAAACAG | AAAGGATATG | TGACAACGCT | GTTGCATCGG | 1440 |
| CGCCGCTATT | TGCCTGATAT | TACAAGCCGC | AATTTCAACG | TCCGCAGTTT | TGCAGAGCGG | 1500 |
| ACGGCCATGA | ACACGCCAAT | TCAAGGAAGC | GCCGCTGACA | TTATTAAAAA | AGCGATGATT | 1560 |
| GATTTAGCGG | CACGGCTGAA | AGAAGAGCAG | CTTCAGGCTC | GTCTTTTGCT | GCAAGTGCAT | 1620 |
| GACGAGCTCA | TTTTGGAAGC | GCCAAAAGAG | GAAATTGAGC | GATTATGTGA | GCTTGTTCCG | 1680 |
| GAAGTGATGG | AGCAGGCCGT | TACGCTCCGC | GTGCCGCTGA | AAGTCGACTA | CCATTACGGC | 1740 |
| CCAACATGGT | ATGATGCCAA | ATAA | | | | 1764 |

( 2 ) INFORMATION FOR SEQ ID NO:2:

( i ) SEQUENCE CHARACTERISTICS:
        ( A ) LENGTH: 587 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
    Ala   Glu   Gly   Glu   Lys   Pro   Leu   Glu   Glu   Met   Glu   Phe   Ala   Ile   Val   Asp
    1                       5                             10                            15

Val   Ile   Thr   Glu   Glu   Met   Leu   Ala   Asp   Lys   Ala   Ala   Leu   Val   Val   Glu
```

-continued

|     |     |     | 20  |     |     | 25  |     |     |     |     | 30  |     |     |     |
|-----|-----|-----|-----|-----|-----|-----|-----|-----|-----|-----|-----|-----|-----|-----|
| Val | Met | Glu | Glu | Asn | Tyr | His | Asp | Ala | Pro | Ile | Val | Gly | Ile | Ala | Leu |
|     |     | 35  |     |     |     | 40  |     |     |     |     | 45  |     |     |     |
| Val | Asn | Glu | His | Gly | Arg | Phe | Phe | Met | Arg | Pro | Glu | Thr | Ala | Leu | Ala |
| 50  |     |     |     |     | 55  |     |     |     |     | 60  |     |     |     |     |
| Asp | Ser | Gln | Phe | Leu | Ala | Trp | Leu | Ala | Asp | Glu | Thr | Lys | Lys | Lys | Ser |
| 65  |     |     |     |     | 70  |     |     |     | 75  |     |     |     |     | 80  |
| Met | Phe | Asp | Ala | Lys | Arg | Ala | Val | Val | Ala | Leu | Lys | Trp | Lys | Gly | Ile |
|     |     |     |     | 85  |     |     |     |     | 90  |     |     |     |     | 95  |
| Glu | Leu | Arg | Gly | Val | Ala | Phe | Asp | Leu | Leu | Leu | Ala | Ala | Tyr | Leu | Leu |
|     |     |     | 100 |     |     |     |     | 105 |     |     |     |     | 110 |     |
| Asn | Pro | Ala | Gln | Asp | Ala | Gly | Asp | Ile | Ala | Ala | Val | Ala | Lys | Met | Lys |
|     |     |     | 115 |     |     |     | 120 |     |     |     |     | 125 |     |     |
| Gln | Tyr | Glu | Ala | Val | Arg | Ser | Asp | Glu | Ala | Val | Tyr | Gly | Lys | Gly | Val |
|     |     | 130 |     |     |     |     | 135 |     |     |     |     | 140 |     |     |
| Lys | Arg | Ser | Leu | Pro | Asp | Glu | Gln | Thr | Leu | Ala | Glu | His | Leu | Val | Arg |
| 145 |     |     |     |     | 150 |     |     |     |     | 155 |     |     |     |     | 160 |
| Lys | Ala | Ala | Ala | Ile | Trp | Ala | Leu | Glu | Gln | Pro | Phe | Met | Asp | Asp | Leu |
|     |     |     |     | 165 |     |     |     |     | 170 |     |     |     |     | 175 |     |
| Arg | Asn | Asn | Glu | Gln | Asp | Gln | Leu | Leu | Thr | Lys | Leu | Glu | His | Ala | Leu |
|     |     |     | 180 |     |     |     |     | 185 |     |     |     |     | 190 |     |
| Ala | Ala | Ile | Leu | Ala | Glu | Met | Glu | Phe | Thr | Gly | Val | Asn | Val | Asp | Thr |
|     |     |     | 195 |     |     |     | 200 |     |     |     |     | 205 |     |     |
| Lys | Arg | Leu | Glu | Gln | Met | Gly | Ser | Glu | Leu | Ala | Glu | Gln | Leu | Arg | Ala |
|     |     | 210 |     |     |     |     | 215 |     |     |     |     | 220 |     |     |
| Ile | Glu | Gln | Arg | Ile | Tyr | Glu | Leu | Ala | Gly | Gln | Glu | Phe | Asn | Ile | Asn |
| 225 |     |     |     |     | 230 |     |     |     |     | 235 |     |     |     |     | 240 |
| Ser | Pro | Lys | Gln | Leu | Gly | Val | Ile | Leu | Phe | Glu | Lys | Leu | Gln | Leu | Pro |
|     |     |     |     | 245 |     |     |     |     | 250 |     |     |     |     | 255 |     |
| Val | Leu | Lys | Lys | Thr | Lys | Thr | Gly | Tyr | Ser | Thr | Ser | Ala | Asp | Val | Leu |
|     |     |     |     | 260 |     |     |     | 265 |     |     |     |     | 270 |     |     |
| Glu | Lys | Leu | Ala | Pro | His | His | Glu | Ile | Val | Glu | Asn | Ile | Leu | His | Tyr |
|     |     | 275 |     |     |     |     | 280 |     |     |     |     | 285 |     |     |     |
| Arg | Gln | Leu | Gly | Lys | Leu | Gln | Ser | Thr | Tyr | Ile | Glu | Gly | Leu | Leu | Lys |
|     | 290 |     |     |     |     | 295 |     |     |     |     | 300 |     |     |     |     |
| Val | Val | Arg | Pro | Asp | Thr | Gly | Lys | Val | His | Thr | Met | Phe | Asn | Gln | Ala |
| 305 |     |     |     |     | 310 |     |     |     |     | 315 |     |     |     |     | 320 |
| Leu | Thr | Gln | Thr | Gly | Arg | Leu | Ser | Ser | Ala | Glu | Pro | Asn | Leu | Gln | Asn |
|     |     |     |     | 325 |     |     |     |     | 330 |     |     |     |     | 335 |     |
| Ile | Pro | Ile | Arg | Leu | Glu | Glu | Gly | Arg | Lys | Ile | Arg | Gln | Ala | Phe | Val |
|     |     |     | 340 |     |     |     |     | 345 |     |     |     |     | 350 |     |     |
| Pro | Ser | Glu | Pro | Asp | Trp | Leu | Ile | Phe | Ala | Ala | Asp | Tyr | Ser | Gln | Ile |
|     |     | 355 |     |     |     |     | 360 |     |     |     |     | 365 |     |     |     |
| Glu | Leu | Arg | Val | Leu | Ala | His | Ile | Ala | Asp | Asp | Asn | Leu | Ile | Glu |
|     |     | 370 |     |     |     |     | 375 |     |     |     |     | 380 |     |     |     |
| Ala | Phe | Gln | Arg | Asp | Leu | Asp | Ile | His | Thr | Lys | Thr | Ala | Met | Asp | Ile |
| 385 |     |     |     |     |     | 390 |     |     |     |     | 395 |     |     |     | 400 |
| Phe | Gln | Leu | Ser | Glu | Glu | Glu | Val | Thr | Ala | Asn | Met | Arg | Arg | Gln | Ala |
|     |     |     |     | 405 |     |     |     |     | 410 |     |     |     |     | 415 |     |
| Lys | Ala | Val | Asn | Phe | Gly | Ile | Val | Tyr | Gly | Ile | Ser | Asp | Tyr | Gly | Leu |
|     |     |     | 420 |     |     |     |     | 425 |     |     |     |     | 430 |     |     |
| Ala | Gln | Asn | Leu | Asn | Ile | Thr | Arg | Lys | Glu | Ala | Ala | Glu | Phe | Ile | Glu |
|     |     |     |     | 435 |     |     |     |     | 440 |     |     |     |     | 445 |     |

```
Arg  Tyr  Phe  Ala  Ser  Phe  Pro  Gly  Val  Lys  Gln  Tyr  Met  Glu  Asn  Ile
     450                      455                      460

Val  Gln  Glu  Ala  Lys  Gln  Lys  Gly  Tyr  Val  Thr  Thr  Leu  Leu  His  Arg
465                      470                      475                      480

Arg  Arg  Tyr  Leu  Pro  Asp  Ile  Thr  Ser  Arg  Asn  Phe  Asn  Val  Arg  Ser
                    485                      490                      495

Phe  Ala  Glu  Arg  Thr  Ala  Met  Asn  Thr  Pro  Ile  Gln  Gly  Ser  Ala  Ala
               500                      505                      510

Asp  Ile  Ile  Lys  Lys  Ala  Met  Ile  Asp  Leu  Ala  Ala  Arg  Leu  Lys  Glu
          515                      520                      525

Glu  Gln  Leu  Gln  Ala  Arg  Leu  Leu  Leu  Gln  Val  His  Asp  Glu  Leu  Ile
     530                      535                      540

Leu  Glu  Ala  Pro  Lys  Glu  Glu  Ile  Glu  Arg  Leu  Cys  Glu  Leu  Val  Pro
545                      550                      555                      560

Glu  Val  Met  Glu  Gln  Ala  Val  Thr  Leu  Arg  Val  Pro  Leu  Lys  Val  Asp
               565                      570                      575

Tyr  His  Tyr  Gly  Pro  Thr  Trp  Tyr  Asp  Ala  Lys
               580                      585
```

( 2 ) INFORMATION FOR SEQ ID NO:3:

( i ) SEQUENCE CHARACTERISTICS:
( A ) LENGTH: 1770 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

```
ATGGAAGCCA   AAGGGAGAA    ACCGCTTGAG   GAGATGGAGT   TTGCCATCGT   TGACGTCATT        60
ACCGAAGAGA   TGCTTGCCGA   CAAGGCAGCG   CTTGTCGTTG   AGGTGATGGA   AGAAAACTAC       120
CACGATGCCC   CGATTGTCGG   AATCGCACTA   GTGAACGAGC   ATGGGCGATT   TTTTATGCGC       180
CCGGAGACCG   CGCTGGCTGA   TTCGCAATTT   TTAGCATGGC   TTGCCGATGA   AACGAAGAAA       240
AAAAGCATGT   TTGACGCCAA   GCGGGCAGTC   GTTGCCTTAA   AGTGGAAAGG   AATTGAGCTT       300
CGCGGCGTCG   CCTTTGATTT   ATTGCTCGCT   GCCTATTTGC   TCAATCCGGC   TCAAGATGCC       360
GGCGATATCG   CTGCGGTGGC   GAAAATGAAA   CAATATGAAG   CGGTGCGGTC   GGATGAAGCG       420
GTCTATGGCA   AAGGCGTCAA   GCGGTCGCTG   CCGGACGAAC   AGACGCTTGC   TGAGCATCTC       480
GTTCGCAAAG   CGGCAGCCAT   TTGGGCGCTT   GAGCAGCCGT   TTATGGACGA   TTTGCGGAAC       540
AACGAACAAG   ATCAATTATT   AACGAAGCTT   GAGCACGCGC   TGGCGGCGAT   TTTGGCTGAA       600
ATGGAATTCA   CTGGGGTGAA   CGTGGATACA   AAGCGGCTTG   AACAGATGGG   TTCGGAGCTC       660
GCCGAACAAC   TGCGTGCCAT   CGAGCAGCGC   ATTTACGAGC   TAGCCGGCCA   AGAGTTCAAC       720
ATTAACTCAC   CAAAACAGCT   CGGAGTCATT   TTATTTGAAA   AGCTGCAGCT   ACCGGTGCTG       780
AAGAAGACGA   AAACAGGCTA   TTCGACTTCG   GCTGATGTGC   TTGAGAAGCT   TGCGCCGCAT       840
CATGAAATCG   TCGAAAACAT   TTTGCATTAC   CGCCAGCTTG   GCAAACTGCA   ATCAACGTAT       900
ATTGAAGGAT   TGTTGAAAGT   TGTGCGCCCT   GATACCGGCA   AAGTGCATAC   GATGTTCAAC       960
CAAGCGCTGA   CGCAAACTGG   GCGGCTCAGC   TCGGCCGAGC   CGAACTTGCA   AAACATTCCG      1020
ATTCGGCTCG   AAGAGGGGCG   GAAAATCCGC   CAAGCGTTCG   TCCCGTCAGA   GCCGGACTGG      1080
CTCATTTTCG   CCGCCGATTA   CTCACAAATT   GAATTGCGCG   TCCTCGCCCA   TATCGCCGAT      1140
GACGACAATC   TAATTGAAGC   GTTCCAACGC   GATTTGGATA   TTCACACAAA   AACGGCGATG      1200
```

```
GACATTTTCC  AGTTGAGCGA  AGAGGAAGTC  ACGGCCAACA  TGCGCCGCCA  GGCAAAGGCC    1260

GTTAACTTCG  GTATCGTTTA  CGGAATTAGC  GATTACGGAT  TGGCGCAAAA  CTTGAACATT    1320

ACGCGCAAAG  AAGCTGCCGA  ATTTATCGAA  CGTTACTTCG  CCAGCTTTCC  GGGCGTAAAG    1380

CAGTATATGG  AAAACATAGT  GCAAGAAGCG  AAACAGAAAG  GATATGTGAC  AACGCTGTTG    1440

CATCGGCGCC  GCTATTTGCC  TGATATTACA  AGCCGCAATT  TCAACGTCCG  CAGTTTTGCA    1500

GAGCGGACGG  CCATGAACAC  GCCAATTCAA  GGAAGCGCCG  CTGACATTAT  TAAAAAAGCG    1560

ATGATTGATT  TAGCGGCACG  GCTGAAAGAA  GAGCAGCTTC  AGGCTCGTCT  TTTGCTGCAA    1620

GTGCATGACG  AGCTCATTTT  GGAAGCGCCA  AAAGAGGAAA  TTGAGCGATT  ATGTGAGCTT    1680

GTTCCGGAAG  TGATGGAGCA  GGCCGTTACG  CTCCGCGTGC  CGCTGAAAGT  CGACTACCAT    1740

TACGGCCCAA  CATGGTATGA  TGCCAAATAA                                        1770
```

(2) INFORMATION FOR SEQ ID NO:4:

(i) SEQUENCE CHARACTERISTICS:
        (A) LENGTH: 589 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met  Glu  Ala  Lys  Gly  Glu  Lys  Pro  Leu  Glu  Glu  Met  Glu  Phe  Ala  Ile
 1              5                        10                       15

Val  Asp  Val  Ile  Thr  Glu  Glu  Met  Leu  Ala  Asp  Lys  Ala  Ala  Leu  Val
               20                   25                       30

Val  Glu  Val  Met  Glu  Glu  Asn  Tyr  His  Asp  Ala  Pro  Ile  Val  Gly  Ile
          35                        40                       45

Ala  Leu  Val  Asn  Glu  His  Gly  Arg  Phe  Phe  Met  Arg  Pro  Glu  Thr  Ala
     50                        55                       60

Leu  Ala  Asp  Ser  Gln  Phe  Leu  Ala  Trp  Leu  Ala  Asp  Glu  Thr  Lys  Lys
65                        70                       75                       80

Lys  Ser  Met  Phe  Asp  Ala  Lys  Arg  Ala  Val  Ala  Leu  Lys  Trp  Lys
                    85                        90                       95

Gly  Ile  Glu  Leu  Arg  Gly  Val  Ala  Phe  Asp  Leu  Leu  Ala  Ala  Tyr
                    100                       105                      110

Leu  Leu  Asn  Pro  Ala  Gln  Asp  Ala  Gly  Asp  Ile  Ala  Ala  Val  Ala  Lys
               115                       120                      125

Met  Lys  Gln  Tyr  Glu  Ala  Val  Arg  Ser  Asp  Glu  Ala  Val  Tyr  Gly  Lys
     130                       135                      140

Gly  Val  Lys  Arg  Ser  Leu  Pro  Asp  Glu  Gln  Thr  Leu  Ala  Glu  His  Leu
145                       150                      155                      160

Val  Arg  Lys  Ala  Ala  Ala  Ile  Trp  Ala  Leu  Glu  Gln  Pro  Phe  Met  Asp
                    165                       170                      175

Asp  Leu  Arg  Asn  Asn  Glu  Gln  Asp  Gln  Leu  Leu  Thr  Lys  Leu  Glu  His
                    180                       185                      190

Ala  Leu  Ala  Ala  Ile  Leu  Ala  Glu  Met  Glu  Phe  Thr  Gly  Val  Asn  Val
               195                       200                      205

Asp  Thr  Lys  Arg  Leu  Glu  Gln  Met  Gly  Ser  Glu  Leu  Ala  Glu  Gln  Leu
     210                       215                      220

Arg  Ala  Ile  Glu  Gln  Arg  Ile  Tyr  Glu  Leu  Ala  Gly  Gln  Glu  Phe  Asn
225                       230                      235                      240

Ile  Asn  Ser  Pro  Lys  Gln  Leu  Gly  Val  Ile  Leu  Phe  Glu  Lys  Leu  Gln
                    245                       250                      255
```

| | | | | | | | | | | | | | | | |
|---|---|---|---|---|---|---|---|---|---|---|---|---|---|---|---|
|Leu|Pro|Val|Leu<br>260|Lys|Lys|Thr|Lys<br>265|Thr|Gly|Tyr|Ser|Thr<br>270|Ser|Ala|Asp|
|Val|Leu|Glu<br>275|Lys|Leu|Ala|Pro|His<br>280|His|Glu|Ile|Val|Glu<br>285|Asn|Ile|Leu|
|His|Tyr<br>290|Arg|Gln|Leu|Gly|Lys<br>295|Leu|Gln|Ser|Thr|Tyr<br>300|Ile|Glu|Gly|Leu|
|Leu<br>305|Lys|Val|Val|Arg|Pro<br>310|Asp|Thr|Gly|Lys|Val<br>315|His|Thr|Met|Phe|Asn<br>320|
|Gln|Ala|Leu|Thr|Gln<br>325|Thr|Gly|Arg|Leu|Ser<br>330|Ser|Ala|Glu|Pro|Asn<br>335|Leu|
|Gln|Asn|Ile|Pro<br>340|Ile|Arg|Leu|Glu|Glu<br>345|Gly|Arg|Lys|Ile|Arg<br>350|Gln|Ala|
|Phe|Val|Pro<br>355|Ser|Glu|Pro|Asp|Trp<br>360|Leu|Ile|Phe|Ala|Ala<br>365|Asp|Tyr|Ser|
|Gln|Ile|Glu<br>370|Leu|Arg|Val|Leu<br>375|Ala|His|Ile|Ala|Asp<br>380|Asp|Asn|Leu|
|Ile|Glu|Ala|Phe|Gln|Arg<br>390|Asp|Leu|Asp|Ile|His<br>395|Thr|Lys|Thr|Ala|Met<br>400|
|Asp|Ile|Phe|Gln|Leu<br>405|Ser|Glu|Glu|Glu|Val<br>410|Thr|Ala|Asn|Met|Arg<br>415|Arg|
|Gln|Ala|Lys|Ala<br>420|Val|Asn|Phe|Gly|Ile<br>425|Val|Tyr|Gly|Ile|Ser<br>430|Asp|Tyr|
|Gly|Leu|Ala<br>435|Gln|Asn|Leu|Asn|Ile<br>440|Thr|Arg|Lys|Glu|Ala<br>445|Ala|Glu|Phe|
|Ile|Glu<br>450|Arg|Tyr|Phe|Ala|Ser<br>455|Phe|Pro|Gly|Val|Lys<br>460|Gln|Tyr|Met|Glu|
|Asn<br>465|Ile|Val|Gln|Glu|Ala<br>470|Lys|Gln|Lys|Gly|Tyr<br>475|Val|Thr|Thr|Leu|Leu<br>480|
|His|Arg|Arg|Arg|Tyr<br>485|Leu|Pro|Asp|Ile|Thr<br>490|Ser|Arg|Asn|Phe|Asn<br>495|Val|
|Arg|Ser|Phe|Ala<br>500|Glu|Arg|Thr|Ala|Met<br>505|Asn|Thr|Pro|Ile|Gln<br>510|Gly|Ser|
|Ala|Ala|Asp<br>515|Ile|Ile|Lys|Lys|Ala<br>520|Met|Ile|Asp|Leu|Ala<br>525|Ala|Arg|Leu|
|Lys|Glu<br>530|Glu|Gln|Leu|Gln|Ala<br>535|Arg|Leu|Leu|Leu|Gln<br>540|Val|His|Asp|Glu|
|Leu<br>545|Ile|Leu|Glu|Ala|Pro<br>550|Lys|Glu|Glu|Ile|Glu<br>555|Arg|Leu|Cys|Glu|Leu<br>560|
|Val|Pro|Glu|Val|Met<br>565|Glu|Gln|Ala|Val|Thr<br>570|Leu|Arg|Val|Pro|Leu<br>575|Lys|
|Val|Asp|Tyr|His<br>580|Tyr|Gly|Pro|Thr|Trp<br>585|Tyr|Asp|Ala|Lys| | | |

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CATTTTGCTG CCGGTCA        17

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GTAAAACGAC GGCCAGTCTT     20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GTAAAACGAC GGCCAGTCGG     20

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CATTTTCGTG CCGGTCAGA     19

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Met Lys Lys Lys Leu Val Leu Ile Asp Gly Asn Ser Val Ala Tyr
1                  5                            10                     15

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Glu Lys Pro Leu Leu Glu Met Arg Phe Cys Ile Val Asp
1                  5                            10

( 2 ) INFORMATION FOR SEQ ID NO:11:

( i ) SEQUENCE CHARACTERISTICS:

( A ) LENGTH: 52 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

ATCTCGGATC CATGAAAAAA AAACTAGTGC TAATCGACGG AAATTCCGTC GC    52

( 2 ) INFORMATION FOR SEQ ID NO:12:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

ATAGAGTCGA CAATGCAGAA GCGCATTTCT AGTAGGGGTT TTTC    44

( 2 ) INFORMATION FOR SEQ ID NO:13:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

AAACCATGGA ATTCATGGAA GCCAAAGGGG AGAAACCGCT TGAGGAG    47

( 2 ) INFORMATION FOR SEQ ID NO:14:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:14:

AAAGGATCCT CTAGAATTGG CCGGCCCGTT TCCG    34

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:15:

GTAAAACGAC GGCCAGT    17